United States Patent [19]

Franz et al.

[11] Patent Number: 5,232,704
[45] Date of Patent: Aug. 3, 1993

[54] SUSTAINED RELEASE, BILAYER BUOYANT DOSAGE FORM

[75] Inventors: Michel R. Franz; Marianne P. Oth, both of Brussels, Belgium

[73] Assignee: G. D. Searle & Co., Chicago, Ill.

[21] Appl. No.: 629,918

[22] Filed: Dec. 19, 1990

[51] Int. Cl.$^5$ .......................... A61K 9/52; A61K 9/48
[52] U.S. Cl. ..................................... 424/456; 424/451
[58] Field of Search ............... 424/451, 456, 472, 488, 424/494, 469; 514/926, 927

[56] References Cited

U.S. PATENT DOCUMENTS

| | | | |
|---|---|---|---|
| 3,574,820 | 4/1971 | Johnson et al. | 424/22 |
| 3,965,143 | 6/1976 | Collins et al. | 260/468 |
| 3,976,764 | 8/1976 | Watanabe et al. | 424/19 |
| 4,060,691 | 11/1977 | Collins et al. | 560/121 |
| 4,088,798 | 5/1978 | Michaelis | 424/472 |
| 4,126,672 | 11/1978 | Sheth et al. | 424/22 |
| 4,140,755 | 2/1979 | Sheth et al. | 424/21 |
| 4,167,558 | 9/1979 | Sheth et al. | 424/22 |
| 4,301,146 | 11/1981 | Sanvordecker | 424/80 |
| 4,331,688 | 5/1982 | Kluender et al. | 514/691 |
| 4,389,393 | 6/1983 | Schor et al. | 424/19 |
| 4,540,566 | 9/1985 | Davis et al. | 424/22 |
| 4,814,178 | 3/1989 | Bolton et al. | 424/467 |
| 4,833,157 | 5/1989 | Kluender et al. | 514/927 |
| 4,857,505 | 8/1989 | Arendt | 514/2 |
| 4,857,506 | 8/1989 | Tyle | 514/12 |
| 4,871,548 | 10/1989 | Edgren et al. | 424/488 |
| 4,937,079 | 6/1990 | Farolfi et al. | 424/488 |
| 5,002,772 | 3/1991 | Curatolo et al. | 424/469 |
| 5,015,481 | 5/1991 | Franz et al. | 424/494 |

FOREIGN PATENT DOCUMENTS

| | | |
|---|---|---|
| 0050480 | 4/1982 | European Pat. Off. |
| 0198769 | 10/1986 | European Pat. Off. |
| 0235718 | 2/1987 | European Pat. Off. |
| WO85/04100 | 9/1985 | PCT Int'l Appl. |
| WO87/00044 | 1/1987 | PCT Int'l Appl. |
| 2097676 | 11/1982 | United Kingdom |
| 2163648 | 3/1986 | United Kingdom |
| 2203338 | 10/1988 | United Kingdom |

OTHER PUBLICATIONS

Timmermans, et al. Gastric Residence Time Determination of Controlled Released Society Aug. 1989.

*Primary Examiner*—Thurman K. Page
*Attorney, Agent, or Firm*—Roger A. Williams; Paul D. Matukaitis

[57] ABSTRACT

Disclosed is a sustained release pharmaceutical dosage form including a drug and adapted to release the drug over an extended period of time. The dosage form comprises a capsule including a non-compressed bi-layer formulation; one layer comprising a drug release layer and the other a buoyant or floating layer, the pharmaceutical dosage form providing extended gastric residence time of the bi-layer formulation so that substantially all of the drug is released in the stomach over an extended period. The dosage form has a large diameter in relation to its size and an initial density of less than 1. The floating layer of the described pharmaceutical dosage form is formulated to provide buoyancy to the dosage form and diametral increase, the floating layer including a polymer which has the properties of a gelling agent and which upon contact with gastric fluid hydrates and forms a gelatinous barrier. The pharmaceutical dosage form is buoyant in gastric fluid for a period up to about 13 hours.

10 Claims, No Drawings

SUSTAINED RELEASE, BILAYER BUOYANT DOSAGE FORM

BACKGROUND OF THE INVENTION

In the treatment of a patient by the administration of oral medication it is desirable to administer a single dose of the selected drug, the drug being released over an extended of period of time rather than administering several doses at regular intervals. Many sustained release formulations are known in the pharmaceutical art, which formulations are intended to continuously provide drug for absorption while the dosage form passes through the gastrointestinal tract of the patient. The conventional oral dosage form generally releases the active compound in a period of a few minutes to 2 hours after administration, making repeated administration of the dosage form necessary. Thus a sustained release formulation which releases the drug over an extended period of time can be advantageous. However, conventional sustained released formulations which are not retained in the stomach and which release the drug in the intestine are not suitable for medicaments which are principally absorbed from the stomach such as acidic medicament, antacids or prostaglandins.

Prostaglandins are involved in the treatment of the pathogenesis of peptic ulcer disease. They inhibit gastric secretion in man. These antisecretory effects appear to involve a direct action on stomach parietal cells. A bilayer floating dosage form is proposed to improve stomachal delivery of prostaglandins or derivatives thereof and misoprostol in particular. This should reinforce local action of prostaglandins on the parietal cells and reduce any side effects appearing when the drug is massively delivered in the intestine. Peak effects of prostaglandins will be lowered while continuously providing drug at the action sites.

Several patents describe buoyant dosage forms which improve gastric residence time. Most of these patents disclose monolithic type of dosage forms. U.S. Pat. No. 4,126,672 and U.S. Pat. No. 4,167,558 describe hydrodynamically balanced capsules with a density of less than one that remain buoyant on the gastric fluid. Hydroxypropyl methyl-cellulose (HPMC) and fatty materials are used to regulate flotation and drug release. U.S. Pat. Nos. 4,814,178 and 4,814,179 describe a non-compressed sustained release floating tablet including a hydrocolloid gelling agent, an inert oil, selected therapeutic agents and water and have a network of multitudinous airholes and passages therein and a density of less than 1. U.S. Pat. No. 4,126,672 describes a buoyant capsule dosage form in which HPMC provides the sustained release. The density of the capsules is adjusted by the use of a fatty material so that the capsules float in the gastric fluid. International application No. W085/04100 describes a gastrointestinal sustained release pharmaceutical unit dosage form comprising a non-compressed mixture of a therapeutic agent and a high molecular weight HPMC contained in a gelatin capsule. The formulations employed in this dosage form are described as not tailored to insure buoyancy in gastric fluids and are said to provide sustained release of drug independent of gastro intestinal pH and therefore equally effective both in the stomach and intestine.

A two layer buoyant tablet containing antacids is disclosed in U.S. Pat. No. 4,140,755. In this patent, one layer is formulated to immediately release the active drug and the other layer to acquire a density lower than one in gastric juice and to provide a sustained release of the active drug.

In vivo investigations have been conducted by different investigators, using non-invasive imaging techniques to determine the gastric residence time of the floating dosage form. Conflicting data are reported on the influence of density on the gastric residence time of a dosage form, some authors showing an increased residence time with floating dosage forms, other authors showing equivalence between floating and non-floating dosage form (S. A. Müller-Lisner and A. L. Blum; The new England Journal of Medicine, 304 (22) 1981; P. R. Sheth and J. Tossounian, Drug Dev. Ind. Pharm., 10(2), 313-339 (1984); W. Erni and K. Held Eur. Neurol. 27:suppll. 1 21-27 (1987); N. Mazer et al. J. of Pharm. Sci., 77 (8) 647-657 (1988); H. M. Ingani et al., Int. J. Pharm.,. 35 157-164 (1987); S. Sangekar et al., Int. J. Pharm.; 35 187-191 (1987); J. Timmermans et al., 5th International Conference on pharmaceutical Technology APGI, 1 42-51 (1989)).

It is believed the gastric residence time of a buoyant unit not only depends on the initial density but, just as importantly, on the evolution of the density as a function of time.

Other authors have shown that the gastric residence time not only depends on buoyancy of the dosage form but also on the dosage form diameter (R. Khosla et al., Int. J. of Pharm., 53 107-117 (1989); J. Timmermans et al.; 5th International Conference on Pharmaceutical Technology APGI, 1 42-51 (1989)). In vivo studies performed with buoyant units indicate that a mean gastric residence time ranging between 3 and 4 hours can be obtained with fed subjects if the dosage form has appropriate floating capabilities, a diametral size of at least 8 to 10 mm and does not disintegrate. The concept has been applied to a tablet which swells upon contact with gastric juice, impeding passing through the pylorus opening. This tablet is not described as being buoyant (U.S. Pat. No. 3,574,820).

SUMMARY OF THE INVENTION

The present invention comprises a sustained release pharmaceutical dosage form including a drug and adapted to release the drug over an extended period of time. The dosage form comprises a capsule including a non-compressed bi-layer formulation; one layer comprising a drug release layer and the other a buoyant or floating layer, the pharmaceutical dosage form providing extended gastric residence time of the bi-layer formulation so that substantially all of the drug is released in the stomach over an extended period. The dosage form has a large diameter in relation to its size and an initial density of less than 1. The floating layer of the described pharmaceutical dosage form is formulated to provide buoyancy to the dosage form and diametral increase, the floating layer including a polymer which has the properties of a gelling agent and which upon contact with gastric fluid hydrates and forms a gelatinous barrier or mass. The pharmaceutical dosage form is buoyant in gastric fluid for a period up to about 13 hours.

The stomach directed drug delivery system of the present invention is conceptually designed to optimize gastric delivery of prostaglandins. Using a monolithic type of dosage form, the release rate is limited by the overall floating characteristics. In bilayer floating capsules wherein the optimized buoyancy formulation layer is separate from the drug release formulation layer, a greater flexibility is possible in release profile adjustment. The drug layer can release the active compound by any means such as diffusion or erosion. The floating layer is designed to carry the release layer and has optimized floating properties as well as diametral size.

DETAILED DESCRIPTION OF THE INVENTION

The present invention comprises a sustained release buoyant pharmaceutical dosage form including a drug and adapted to release the drug over an extended period of time, substantially all of the said drug release taking place within the stomach. The pharmaceutical dosage form comprises an uncompressed bi-layer formulation, one layer comprising a drug release layer and the other layer comprising a buoyant layer. The release layer and the floating layer are formulated to insure cohesion between the two layers for a long period of time. An extended gastric residence time of the bi-layer formulation is provided so that substantially all of the drug is released in the stomach. The uncompressed bi-layer formulation is contained within a capsule which has a relatively large diameter in relation to its size, the pharmaceutical dosage form having an initial density of less than one. Although the dosage form can be utilized with any medicament or drug it is particularly useful for acidic medicaments, prostaglandins and other drugs which are most advantageously released in the stomach.

Some prostaglandin drugs are known to possess anti-ulcerogenic properties. Hence, it is desirable to combine or mix a prostaglandin drug having such properties, such as misoprostol, with aspirin or a non-steroidal anti-inflammatory drug (NSAID) which oftentimes exhibit ulcerogenic side effects.

Acceptable prostaglandins for use herein include prostaglandins having the following structure

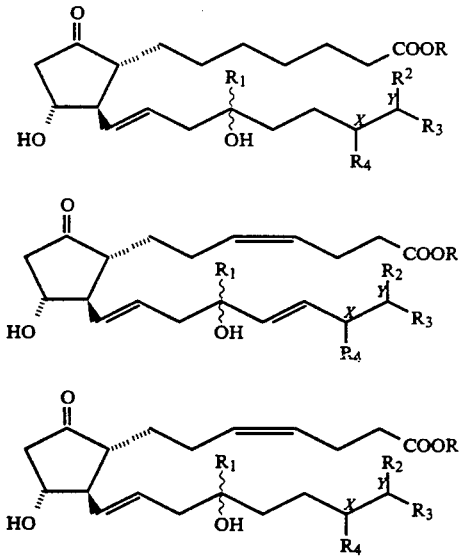

wherein R represents hydrogen or lower alkyl having 1 to 6 carbon atoms; $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons and wherein the X—Y bond can be saturated or unsaturated.

Examples of suitable NSAID's to mix or combine with a prostaglandin drug are diclofenac, piroxicam, ibuprofen or naproxen. An example of a suitable combination or mixture is diclofenac in a therapeutic amount such as from about 25 to 75 milligrams and the prostaglandin misoprostol in a therapeutic amount of from about 100 to 200 micrograms.

The invention will be described with respect to an oral pharmaceutical dosage form for the drug misoprostol, a gastric anti-secretory medicament sold under the trademark Cytotec by G. D. Searle, Co. and which is described, in U.S. Pat. No. 4,060,691 issued Nov. 29, 1977. The described uncompressed bi-layer formulation is disposed within a capsule and as hereinafter described, comprises a drug release layer and a buoyant layer. The dosage form is buoyant in gastric fluid, has a large diameter in relation to its size, is non-disintegrating and releases most of the drug content within the first 3 to 4 hours of exposure to the gastric fluid. The drug release layer is disposed within the bottom body of the capsule and the buoyancy layer is disposed within part of the body and the head of the capsule.

In a specific embodiment of the invention, the capsules comprise clear hard gelatin capsules size B such as Coni Supro, available from Capsugel, the length of the capsule being 14.41 mm and the diameter 8.36 mm. The length of the drug release layer within the capsule is 4.61 mm and length of the buoyancy layer is 9.80 mm. The bulk density of the bi-layer formulation within the capsule is 0.738 mg per cubic millimeter. A selected bi-layer formulation for the drug misoprostol is as follows:

| RELEASE LAYER: | | |
|---|---|---|
| MISOPROSTOL 1:100 | 20.2 MG | 14.96% |
| METHOCEL K4M | 4.0 mg | 2.96 |
| LACTOSE FC | 82.03 mg | 60.76 |
| PHARMACOAT 606 | 16.0 mg | 11.85 |
| METHOCEL K100 | 10.0 mg | 7.40 |
| Mg STEARATE | 2.7 mg | 2.00 |
| AEROSIL 200 | 0.07 mg | 0.05 |
| | 135.00 mg | |
| BUOYANT LAYER | | |
| METHOCEL K4M | 200.0 mg | 80% |
| LACTOSE | 37.37 mg | 14.95 |
| Mg STEARATE | 12.5 mg | 5.00 |
| AEROSIL 200 | 0.13 mg | 0.05 |
| | 250.00 mg | |
| CAPSULE: CONI-SNAP SUPRO B | | |

Drug Release Layer

The drug release layer is formulated to release misoprostol in the stomach by both diffusion and erosion of the drug release layer. Hydroxypropyl methylcellulose (HPMC) was used in the formulation. This polymer acts as a gelling agent which upon contact with the liquid fluids, hydrates and forms a gelatinous barrier around the dosage form. This gelatinous layer provides the following properties to the buoyant dosage form:

The powder within the dosage form remains dry for a sustained period of time, the density of the dosage form remaining lower than 1. Diffusion of water through the gelatinous barrier induces an increase of the barrier thickness and an increase of the density.

After dissolution of the gelatin capsule, the shape of the capsule and the cohesion of the two layers are maintained for a sustained period of time due to the formation of the gelatinous barrier or mass.

The release layer is non-disintegrating, there is practically no particulate matter released from the drug layer, which avoids the delivery in the intestine of large particles containing drug.

The polymer is progressively hydrated and the diffusion of water into the dosage form and the diffusion of the drug out of the dosage form controls the release rate of the drug. The thickness of the gelatinous barrier increases as diffusion of water inside the dosage form proceeds.

The gelatinous layer is progressively dissolved which also aids in controlling the release rate of the drug.

Hydration of the polymer induces an increase of the dosage form diameter, which increase of diameter improves gastric resident time of the dosage form. Several grades of hydroxy propylmethyl cellulose (HPMC) were used namely Methocel K4M, (viscosity of 4000 cts for a 2% water solution at 20° C.) and Methocel K100 which are an HPMC of lower viscosity (viscosity of 100 cts for a 2% water solution at 20°) and Pharmacoat 606 or Pharmacoat 603 which are a HPMC of very low viscosity (5 cts and 3 cts for a 2% water solution at 20° C. respectively).

Other gelling agents such as gums, carboxymethylcellulose, gelatin or other hydrocolloids can be used.

Lactose is used as a diluent. Other suitable diluents are mannitol, sorbitol, glucose, microcrystalline cellulose, gelatin, starch, dicalcium phosphate, PVP, and polyethylene glycol. Magnesium stearate is used as a lubricant although other lubricants such as thixcin can be used. A glidant such as colloidal silicone dioxide (Aerosil 200) can be used. Other excipients may be added to modify the release profiles such as: disintegrants, surfactants, salts.

A suitable formulation is as follows:

| | |
|---|---|
| Prostaglandin | 0.01–1% w/w |
| Pharmacoat 606 | 0–80% |
| Methocel K100 | 0–80% |
| Methocel K4M | 0–30% |
| Lactose 100 Mesh | 0–75% |
| Mg Stearate | 1–10% |
| Aerosil 200 | 0.05–2% |

Buoyant Layer

The buoyant layer is formulated to provide buoyancy for the dosage form and to improve diametral increase. A suitable formulation is as follows:

| | |
|---|---|
| Methocel K4M | 30–95% w/w |
| Lactose 100 Mesh | 0–60% |
| Mg Stearate | 0–15% |
| Aerosil 200 | 0.5–2% |

A preferred formulation is as follows:

| Release Layer | | |
|---|---|---|
| Misoprostol/HPMC 1:100 | 20.2 mg | 14.4% |
| Pharmacoat 603 | 60.0 | 42.8 |
| Lactose | 58.4 | 41.7 |
| Stearate Mg | 1.4 | 1.0 |
| | 140 mg | |

| Buoyant Layer | | |
|---|---|---|
| Methocel K4M | 131.5 mg | 73.0% |
| PEG 6000 | 43.0 | 23.8 |
| Stearate Mg | 4.5 | 2.5 |
| Aerosil 200 | 1.0 | 0.56 |
| | 180 mg | |

Capsule: Coni-Snap SuproB.
Density: 0.6 mg/mm$^3$.

To improve the gastric resident time of the buoyant dosage form the diameter should be as large as possible.

Various hydrocolloids of high viscosity can be used such as hydroxypropylmethyl cellulose, other cellulose derivatives, gums, polysaccharides and gelatin. An hydroxypropylmethylcellulose of high viscosity (Methocel K4M) is preferred.

Since the concentration of the HPMC is high the diffusion rate of water into the dosage form is slow so that the overall density remains close to the density of the dry powder. The magnesium stearate improves the buoyancy by improving the cohesion of the gelatinous layer, but other lubricants or fatty materials can be used. The Aerosil 200 acts as a glidant.

Lactose, sorbitol, mannitol, glucose, microcrystalline cellulose, gelatin, starch, dicalcium phosphate, polyethylene glycol, PVP, or fatty materials or others can be used as a diluent.

Other formulation additives may be added such as lubricants, glidants, surfacants, disintegrants, and the like.

HARD GELATIN CAPSULE

Any type of hard gelatin capsule can be used for the bilayer formulations of the present invention. Of special interest are Coni snap Supro capsules (Capsugel Company) which were selected because of their large diameter allowing improved gastric residence time (GRT) while still compatible with patient compliance.

Any container made of any polymer and able to host two separate layers can be used to hold formulations of the present invention.

The density of the final dosage form is always lower than one with a typical range being 0.5–0.9 mg/mm.

METHOD OF PREPARATION

The sustained release, bilayer buoyant dosage form of the present invention can be prepared by methods well established in the art. In one embodiment, the drug release layer comprising the misoprostol, methocel K4M and K100, Pharmacoat 606, lactose and Aerosil 200 are mixed, passed through a 0.7 mm sieve and blended. The Mg stearate is pre-mixed, blended, passed through a 0.7 mm sieve and blended together with the previously blended ingredients.

The buoyant layer comprising Methocel K4M, lactose and Aerosil 200 are mixed, passed through a 0.7 mm sieve and blended. The magnesium stearate is pre-mixed, blended, passed through a 0.7 mm sieve and blended together with the previously blended ingredients.

The drug release layer is filled into the capsule using a conventional filling machine and the buoyancy layer is then added by free flowing the powder mixture into the capsule body. An overfilling of the buoyant layer can be used to minimize mixing of the two layers.

Other conventional techniques can be used such as handfilling, volumetric filling, filling by weighing each layer.

The cohesion between the two layers was tested in the disintegration test using USP modified method (mesh at both sides of basket), test starting with immersion of capsules without agitation for 15 minutes before the normal disintegration test procedure. The two capsule layers did not separate during the test. In addition while the drug release layer progressively eroded as expected during the disintegration test, the buoyancy layer remained monolithic for over 8 hours.

Intragastric misoprostol sustained delivery is believed to improve the efficacy of the product by increasing its local action on the stomach wall while reducing its side effects which appear when the drug is massively delivered in the intestine.

Floating dosage forms have been investigated as a means for delivering Misoprostol in a controlled and sustained manner into the stomach. In vivo studies performed with buoyant units indicate that a mean gastric residence time ranging between 3 and 4 hours can be obtained with fed subjects (light breakfast) if the dosage form has appropriate floating capabilities, a diametral size of at least 8 to 10 mm in a dry state and does not disintegrate (monolithic). By designing a bilayer floating capsule wherein the optimized buoyancy formulation layer is separated from the drug release formulation layer, a greater flexibility of release profile adjustments is obtained.

In vitro and in vivo results obtained with a preselected Misoprostol bilayer capsule are described hereinafter.

γ-Scintigraphic Study I

In vivo study of a placebo-floating bilayer capsule for subjects fed with a light meal.

FORMULATIONS

|  |  | (% w/w) |
|---|---|---|
| Drug Release Layer |  |  |
| Pharmacoat 606 | 36.0 mg | 26.67 |
| Methocel K100 | 10.0 mg | 7.41 |
| Methocel K4M | 4.0 mg | 2.96 |
| Lactose 100 mesh | 82.2 mg | 60.91 |
| Mg stearate | 2.7 mg | 2.00 |
| Aerosil 200 | 0.07 mg | 0.05 |
| Buoyancy layer: |  |  |
| Methocel K4M | 200.0 mg | 80.00 |
| Lactose 100 mesh | 37.4 mg | 14.95 |
| Mg stearate | 12.5 mg | 5.00 |
| Aerosil 200 | 0.1 mg | 0.05 |

A small amount of bromocresol green (BCG) was incorporated into the buoyancy layer in order to enable its visualization during volume kinetics and disintegration assays.

DOSAGE FORMS

Hard gelatin capsules, clear (Coni Snap Supro, Capsugel), size B.
Length: 14.41 mm (length-buoyancy layer: 9.80 mm) (length-drug layer: 4.61 mm).
Diameter: 8.36 mm.
Mean nominal weight±SD: 470.0±1.9 mg.
Volume: 638 mm.
Bulk density of bilayer capsule: 0.738 mg/mm.

DISSOLUTION MEDIA

HCl at pH 1.2+0.05%, Tween 80 (1200 ml, 37.0° C.).
Water a pH 6.0+0.05%, Tween 80 (1200 ml, 37.0° C.).

TEST CONDITIONS

Resultant-weight apparatus: (buoyancy kinetics) no stirring of fluid medium, capsules maintained immersed by spit-holder extremity, 8 hours continuous records.

Microscope system: (volume kinetics) paddle 60 rpm for stirring of fluid medium (except for one triplicate assay performed on the drug layer with no stirring of fluid medium), capsules maintained immersed by spit-holder extremity, measurements at fixed time intervals during 8 hours.

Disintegration: USP modified method (mesh at both sides of basket), test starting with immersion of capsules without agitation during 15 minutes before normal disintegration test procedure.

VOLUME KINETICS OF DRUG LAYER

The volume kinetics determination performed with stirring of the fluid medium indicate a continuous erosion of the drug release layer until its total disappearance. No significant disintegration of this layer was observed.

The drug release layer was found to undergo a faster erosion at pH 1.2 (not measurable after 3 hours) when compared to a pH 6.0 medium (not measurable after 4 hours). This pH-dependent behavior is believed due to the characteristics of the excipient formulation.

The lack of fluid medium stirring greatly affects the erosion rate of the drug layer and is observed to be much slower (volume of drug layer not measurable after 8 hours). This different agitation-dependent eroding behavior is believed due to the characteristics of the excipient formulation and may determine the variability of drug release profiles as a function of external motility (i.e. gastric peristaltism).

For both pH and stirring conditions, the drug release layer did not break away from the buoyancy layer.

VOLUME KINETICS OF BUOYANCY LAYER

A fast volume increase of the buoyancy layer was observed during the 20 first minutes and a continuous but slower swelling is observed up to 8 hours. The volume increase of this layer is observed to be more important at pH 6.0 than at pH 1.2 which confirms the knowledge that HPMC hydrophilic polymers swell better in water than in acidic media. The total volume increase after 8 hours reaches a mean of 300% at pH 1.2 while a more than 400% increase is observed at pH 6.0.

DIAMETRAL SIZE KINETICS OF BUOYANCY LAYER

The diametral size of the buoyancy layer increases from 8.4 to 10 mm within the 10 first minutes. This diametral size enhancement is appropriate with respect to gastric retention of the dosage form.

The swelling differences of the buoyancy layer as a function of fluid pH have a slight and consistent effect on the diametral size evolution. The diametral size after 8 hours was found to be 10.7 mm at pH 1.2 and 11.7 mm at pH 6.0.

DISINTEGRATION OF BILAYER CAPSULE

An amount of buoyancy formulation powder was selected to obtain an over-filling of the capsule and to avoid mixing of the two capsule layers during handling or after immersion.

The two capsule layers of the herein described bilayer capsule did not mix together after a 20 minute friabilator test nor during the USP disintegration test. In addition, while the drug release layer progressively eroded as expected during the disintegration test, the buoyancy layer remained monolithic and showed a mean disintegration time of 29.3 hours. The stability and durability of the described dosage form was found to be optimal at either pH 1.2 or 6.0 for at least 8 hours.

The preselected bilayer capsule having displayed adequate in vitro properties with respect to the requirement for prolonged gastric retention, an in vivo investigation was designed on the basis of the following objectives:

To monitor the intragastric buoyancy of the bilayer capsule as a function of time To determine the gastric residence time of the bilayer capsule To evaluate the cohesion efficacy between the two capsule layers To measure the erosion and shape modification of the drug release layer To gather data on the administration of a bilayer floating dosage form capsule in healthy male volunteers

LABELLING OF BILAYER CAPSULE

Each of the two capsule layers was labelled by a different radiopharmaceutical in order to allow separate visualization and monitoring during the in vivo experiments. Labelling was realized extemporaneously as follows:

Drug release layer: 135 mg formulation homogeneously mixed with 10 mg sodium chloride with the required activity of 111In oxinate deposited, 0.500 mCi.

Buoyancy layer: 250 mg formulation homogeneously mixed with 10 mg Amberlite IR120 ion exchange resin whereon the required activity of 201TI chloride 0.300 mCi.

The in vitro measured activity release profiles of the labelled layers are shown in the following table. (HCl pH 1.2+0.05% Tween 80, 37.0° C., no stirring of fluid medium). 111In incorporated in the drug layer is seen to have a faster release than 201T1 in the buoyancy layer due to the erosion of this layer as a function of time. The 111In release profile appears to be consistent with the erosion profile measured for the drug layer without stirring of the fluid medium as no total activity release is seen to be achieved even after 8 hours.

In vitro measured activity release (mean %) of radiolabels from the drug layer (111In) and the buoyancy layer (201 T1) of the capsule.

TABLE 1

| TIME (HOURS) | % RELEASE | |
|---|---|---|
| | 111In | 201 Tl |
| 1 | 45% | 30% |
| 2 | 58 | 41 |
| 3 | 66 | 50 |
| 4 | 75 | 55 |
| 5 | 78 | 60 |
| 6 | 80 | 66 |
| 7 | 82 | 71 |
| 8 | 85 | 75 |

Conventional scintigraphic monitoring technique was used to obtain the in vivo data. In addition to the dosage form labelling, 99mTc pertechnetate was used to visualize the external emitting markers and was administered to the subjects to visualize the gastric contents at the start and end of the session.

However, to attempt more quantitative measurements of the activity released from the drug layer as a function of time, special attention was given to the selectivity and the specificity of the gamma camera acquisition conditions. The final choice of the following peaks and windows for each of the three radionuclides enabled good visualization and differentiation at any time of the different regions of interest (drug layer — buoyancy layer — gastric contents — external markers) while avoiding significant activity contributions of 99mTc and 201T1 in the images made in 111In conditions (drug layer):

201T1: peak 70 keV±10%
99mTc: peak 132 keV±10%
111In: peak 234 keV±20%

The acquisition time was limited to 10 sec and sequential anterior imaging with a LFOV low energy (140 keV) collimator was obtained every 10 minutes.

STUDY POPULATION AND SUBJECT CONDITIONS

The study population was composed of 10 healthy male volunteers (age: 28-32 years, height: 168-186 cm, weight: 61-83 kg). All subjects were admitted after an overnight fast and ingested a standardized breakfast. They were then not allowed to drink or eat. The subjects remained in an upright position throughout the entire monitoring procedure.

The individual results of scintigraphic monitoring in man are recorded in Table 2 (gastric residence times (GRT) and other time-dependent events). For each subject, the positioning measurements of the two capsule layers inside the GI tract as a function of time as well as a semi-quantitative evaluation of the activity released in vivo from the drug layer has been determined.

TABLE 2

PLACEBO BI-LAYER CAPSULE
INDIVIDUAL RESULTS OF SCINTIGRAPHIC MONITORING IN MAN (N = 10)

| SUBJECT NO | GASTRIC RESIDENCE TIME (GRT) (MIN.) | SEPARATION OF LAYERS (TIME IN MIN.) | DRUG LAYER GRT (MIN.) | BUOYANCY LAYER GRT (MIN.) | PARTIAL SPREAD DRUG LAYER |
|---|---|---|---|---|---|
| 1 | 100 | N | — | — | — |
| 2 | 155 | 171 | — | — | 171 |
| 3 | 205 | N | — | — | 236 |
| 4 | 304 | N | — | — | 341 |
| 5 | 122 | N | — | — | 207 |
| 6 | 291 | N | — | — | 302 |

TABLE 2-continued

PLACEBO BI-LAYER CAPSULE
INDIVIDUAL RESULTS OF SCINTIGRAPHIC MONITORING IN MAN (N = 10)

| SUBJECT NO (MIN.) | GASTRIC RESIDENCE TIME (GRT) (MIN.) | SEPARATION OF LAYERS (TIME IN MIN.) | DRUG LAYER GRT (MIN.) | BUOYANCY LAYER GRT (MIN.) | PARTIAL SPREAD DRUG LAYER |
|---|---|---|---|---|---|
| 7 | 225 | N | — | — | 258 |
| 8 | 195 | N | — | — | 227 |
| 9 | 197 | N | — | — | 283 |
| 10 | — | 78 | 118 | 229 | 129 |
|  | 199 ± 69 |  |  |  |  |

The recorded gastric residence times varied from 100 to 304 min. with a mean±SD of 199±69 min (n=10).

The results of subject No 10 were not taken into account for calculation since the drug and buoyancy layers separated in the stomach (after 78 min.) and were emptied separately. Moreover, the separation of the two layers in subject No 10 showed the drug layer to rapidly sediment in the lower part of the stomach where it was emptied after 118 min., meanwhile the buoyancy layer remained floating in the upper part of the stomach and had, consistently with previous finding about floating systems, a prolonged gastric residence time (229 min.). This accidental separation consequently indicates the preponderant importance of the buoyancy layer attached to the drug delivery system in achieving a enhanced stomachal residence of the product by the intragastric buoyancy process.

The bilayer capsule remained in the upper part of the stomach in all cases throughout its entire gastric residence period, thus in a buoyant state upon the gastric contents. The in vitro measured floating capabilities therefore are reproducible in vivo with subjects in fed conditions.

During the gastric residence period of the bilayer capsule, a separation between the two layers was only observed in one subject out of the study population (No 10, as already described above). This lack of cohesion between the layers is more than likely due to a non-homogeneous hydration of the hydrophilic polymer at the outer surface since, in all in vitro tests performed on the entirely immersed capsule, no separation had been recorded even under powerful dynamic constraints (disintegration test). This lack of hydration could be the consequence of a relatively weak peristaltism occurring in the upper part of the stomach where the capsule remains during the digestive phase. This observation about gastric motility in the fundus is apparently confirmed by the in vivo measured eroding rate of the drug layer (refer hereunder to erosion of drug layer).

The sustained release, bilayer buoyant dosage form of the present invention can be prepared by methods well established in the art. In one embodiment, the drug release layer comprising the misoprostol, methocel K4M and K100, Pharmacoat 606, lactose and Aerosil 200 are mixed, passed through a 0.7 mm sieve and blended. The Mg stearate is pre-mixed, blended, passed through a 0.7 mm sieve and blended together with the previously blended ingredients.

The buoyant layer comprising Methocel K4M, lactose and Aerosil 200 are mixed, passed through a 0.7 mm sieve and blended. The magnesium stearate is pre-mixed, blended, passed through a 0.7 mm sieve and blended together with the previously blended ingredients.

The drug release layer is filled into a capsule without any compaction using a conventional capsule filling machine and the buoyant layer is then added by free flowing the powder mixture into the capsule body. An overfilling of the buoyant layer is used to minimize mixing of the two layers.

γ-Scintigraphic Study II

IN VIVO STUDY OF A PRESELECTED PLACEBO FLOATING BILAYER CAPSULE FOR SUBJECTS FED WITH A SUCCESSION OF MEALS

Study Rationale and Objectives

Various advantages result from delivering misoprostol (Cytotec) continuously inside the stomach over a prolonged period of time.

A formulation of a bilayer capsule was tested in vitro and in vivo; i.e. on healthy human volunteers remaining in an upright position and having taken a breakfast only. Results showed, either in vitro or in vivo, the drug layer of the capsule to progressively erode as intended for drug release purposes. The capsules were seen to effectively remain in a buoyant state upon the gastric contents, and the recorded gastric residence time after a light breakfast was found to range between 3 and 4 hours.

In the present study, the healthy male volunteers were administered a floating bilayer capsule after a more caloric breakfast and were then fed throughout a one day session with a succession of different standardized meals.

Study objectives were:
- To monitor the intragastric buoyancy of the bilayer capsule as a function of time
- To determine the gastric residence time of the bilayer capsule
- To verify the cohesion between the two capsule layers
- To evaluate the rate of erosion process of the drug layer
- To gather safety data on the administration of a bilayer floating capsule in healthy male volunteers

MATERIALS AND METHODS

The formulation, dosage forms, labeling of bilayer capsule and scintigraphic monitoring technique used were the same as described for the γ-Scintigraphic Study I.

STUDY POPULATION

Table 3 shows the demographic data of the study population. In order to allow comparison between this session and the previous one — and since several volunteers participated in both —, Table 3 regroups the entire study population of the two sessions. Each volunteer (n=14) has therefore been given an enrolment number according to his participation in the session with breakfast only (subjects 1 to 10) or to the session with a succession of meals (subjects 11 to 20).

Subject 12 (volunteer C) was retrospectively found to have undergone surgical resection of hiatal hernia three years earlier. Results of this subject were therefore discarded.

MEAL COMPOSITION AND ADMINISTRATION SCHEDULE

The subjects were admitted to the study after an overnight fast and ingested a standardized breakfast at 8:30 a.m. Composition of meals are given in Table 4 (session with breakfast only) and in Table 5 (session with succession of meals). During the latter session, meal administration was continued at fixed time intervals until 6:00 p.m. (see schedule Table 5) at which time the subjects were no longer allowed to eat.

TABLE 3

Demographic data of the study population (n = 14 different healthy male volunteers identified alphabetically by letters A to N) and enrollment sequence of the volunteers in the 2 different study sessions (n = 10 subjects per session; subjects numbered from 1 to 20.

| VOLUN- | DEMOGRAPHIC DATA | | | ENROLLMENT NUMBER | |
|---|---|---|---|---|---|
| TEERS (n = 14) | AGE (years) | HEIGHT (cm) | WEIGHT (kg) | Breakfast only | Succession of meals |
| A | 24 | 182 | 65 | — | 15 |
| B | 28 | 172 | 83 | 2 | — |
| C | 32 | 178 | 67 | — | 12 |
| D | 30 | 178 | 70 | 8 | 20 |
| E | 29 | 175 | 75 | 6 | 18 |
| F | 28 | 178 | 72 | 4 | 17 |
| G | 27 | 178 | 60 | — | 11 |
| H | 28 | 182 | 73 | 5 | — |
| I | 23 | 175 | 73 | — | 14 |
| J | 30 | 172 | 76 | 1 | 16 |
| K | 28 | 178 | 73 | 9 | — |
| L | 30 | 186 | 82 | 10 | 19 |
| M | 31 | 177 | 73 | 7 | — |
| N | 32 | 168 | 61 | 3 | 13 |
| Min. value: | 23 | 186 | 60 | | |
| Max. value: | 32 | 186 | 83 | | |
| Mean: | 28.6 | 177.1 | 71.6 | | |
| ± SD: | 2.6 | 4.4 | 6.5 | | |

TABLE 4

Composition of the standardized breakfast taken by the study subjects after an overnight fast

| Breakfast components | Weight (g) | Energy (kcal) | Lipids (g) | Proteins (g) | Glucids (g) |
|---|---|---|---|---|---|
| croissant | 100 | 577 | 40.0 | 5.8 | 47.0 |
| orange juice | 150 | 76 | — | 1.0 | 19.0 |
| coffee | 150 | — | — | — | — |
| water | 300 | — | — | — | — |
| Total: | 700 100 g solid 600 ml liquid | 653 | 40.0 | 6.8 | 66.0 |

TABLE 5

Composition and time of administration of the different standardized meals taken by the study volunteers during a one day session.

| Time of administration | Mean components | Weight (g) | Volume (ml) | Energy (kcal) |
|---|---|---|---|---|
| 8:30 | BREAKFAST: | 335 | 685 | 1301 |
| | scrambled eggs | 145 | — | 513 |
| | bacon | 50 | — | 226 |
| | white bread | 95 | — | 176 |

TABLE 5-continued

Composition and time of administration of the different standardized meals taken by the study volunteers during a one day session.

| Time of administration | Mean components | Weight (g) | Volume (ml) | Energy (kcal) |
|---|---|---|---|---|
| | butter | 20 | — | 150 |
| | jam | 25 | — | 62 |
| | coffee-milk-sugar | — | 185 | 54 |
| | orange juice | — | 200 | 120 |
| | water | — | 300 | — |
| 11:00 | APPETIZER SNACK: | 72 | 200 | 399 |
| | chips | 30 | — | 156 |
| | cheese bricks | 42 | — | 123 |
| | pineapple juice | — | 200 | 120 |
| 12:00 | LUNCH: | 630 | 815 | 1036 |
| | soup | — | 300 | 114 |
| | chicken leg | 150 | — | 255 |
| | mashed potatoes | 150 | — | 207 |
| | carrots | 150 | — | 110 |
| | bread stick | 55 | — | 129 |
| | butter | 10 | — | 75 |
| | sweet pudding | 115 | — | 92 |
| | coffe-milk-sugar | — | 185 | 54 |
| | fizzy water | — | 330 | — |
| 16:00 | SNACK: | 95 | 185 | 477 |
| | tea-milk-sugar | — | 185 | 54 |
| | chocolate eclair | 95 | — | 423 |
| 18:00 | DINNER: | 585 | 515 | 772 |
| | tagliatelli ham cheese | 400 | — | 404 |
| | bread stick | 55 | — | 129 |
| | butter | 10 | — | 75 |
| | banana | 120 | — | 110 |
| | coffee-milk-sugar | — | 185 | 54 |
| | fizzy water | — | 330 | — |
| | Total: | 1717 | 2400 | 3985 |

STUDY CONDITIONS

After breakfast administration, each subject ingested one floating bilayer capsule with 150 ml water (9:00 a.m.). The subjects were then ambulatory and remained in an upright position, either standing or sitting, during the entire monitoring procedure. Subjects were discharged from the study once their floating capsule could be unequivocally visualized outside the gastric region of interest (ROI). The investigation period was limited to a maximum 15 hours.

RESULTS AND DISCUSSION

The individual results of gastric residence time for the two different sessions are shown in Table 6. More specific results derived from scintigraphic monitoring of the session with a succession of meals appear in Table 7 (separation of layers, total erosion of drug layer, activity remaining in drug layer at time of gastric emptying). The mean±SD volume of low calorie drinks taken by the subjects 11 to 20 between the meals was of 632±275 ml (n=9).

GASTRIC RESIDENCE TIME OF BILAYER CAPSULE

For the session with breakfast only, gastric residence times ranged from 100 to 304 min (mean±SD: 199+69 min, n=9). For the session with a succession of meals, gastric residence times ranged from 398 to more than 900 min for two subjects (mean±SD: 618±208 min, n=9). The succession of meals was found to provide a strong gastric residence time enhancement to the floating forms in comparison with the effects obtained with breakfast only. The shortest gastric residence time of 6 hours and 38 min as well as the mean residence time of about 10 hours seem to be mostly appropriate with regard to the requirements of sustained intragastric misoprostol delivery. The variability of gastric residence time results, assessed by the coefficient of variation, appears to be very similar for the two different sessions (breakfast only: 35%, succession of meals: 34%). No correlation assignable to human factors was found between the gastric residence time results of the two sessions for the subjects who participated to both.

INTRAGASTRIC BUOYANCY OF BILAYER CAPSULE

During the previous session (breakfast only), relative intragastric height measurements obtained for all subjects had already shown the floating bilayer capsules to constantly remain in a buoyant state upon the gastric contents.

In vivo floating capabilities consequently appeared to be suitable, at least with respect to the considered breakfast ingredients. Because this reliable intragastric buoyancy provided an initial residence in the upper part of the stomach, the floating capsules were systematically protected against emptying during the digestive phase and could only be evacuated once the quasi-totality of meal contents had been emptied.

During the last session performed with a succession of meals, all floating bilayer capsules could also be observed, consistently with previous findings, to stay buoyant inside the stomach throughout their entire gastric residence period. None of the administered meals nor administration itself seemed to produce any altering effect on the floating capabilities of the capsules, for instance, by making them abruptly sink through the gastric contents. These additional in vivo results further corroborate the adequacy of floating performances of the in vitro-optimized buoyancy layer formulation. While carrying the attached drug layer, the floating capsule remains reliably buoyant on the gastric contents. Stability as well as durability of floating forces appear to be maintained even when the capsule formulation is confronted with various food-stuffs and drinks or to repeated meal administration.

More specifically in the matter of gastric retention, results indicate that as often as a meal is readministered at the time when the previous digestive phase is not yet completed, the floating capsule still remaining in the stomach is then carried again in the fundus (upper part of the stomach) and is further retained in a buoyant state for an additional digestive phase period. The relative intragastric height of the capsule is seen to progressively decrease as digestive phase proceeds and to rise each time a meal has just been taken.

Since the floating capsule has a residence position which follows the upper level of the gastric contents, it cannot be emptied as long as there is sufficient food in the stomach for the form to float above the gastroduodenal junction. In such conditions, the gastric residence time of the form mainly depends on the solid/liquid meal emptying rate (variability of subject) and on the time interval between meal readministrations (fixed by experimentation). During the present investigation, no subject emptied its floating capsule before the lunch. This is more than likely due to the high caloric contents of the breakfast and to the short time intervals separating the three first meals (breakfast/appetizer snack/lunch). Two subjects (No 13, 18) emptied their dosage forms about 3 hours and 40 min after lunch, i.e. just before the 4:00 p.m. snack. The contribution of this light snack to digestive phase extension was insufficient for three subjects (No 16, 17, 20) to enable them to reach dinner time with the capsule still residing in the stomach. Out of the four remaining subjects who passed beyond dinner, two subjects emptied their capsules about 3 hours (No 19) and 4 hours (No 14) after dinner, meanwhile the two last subjects (No 11, 15) were discharged from the study at 12:00 p.m. without having evacuated their floating capsules from the stomach (6 hours after dinner, total gastric residence time superior to 15 hours).

It may hence be concluded, as far as prolonged gastric retention is concerned, that:
- a reliable gastric retention process bilayer is obtainable because of the intragastric buoyancy of an optimized floating dosage form,
- the floating form should preferably be ingested after the heaviest meal of the day,
- to further enhance gastric retention of the form, meals should be taken at regular time intervals and fasting periods should never be too long.

COHESION BETWEEN BUOYANCY AND DRUG LAYERS

While remaining in the stomach, floating capsules were repeatedly submitted to the mechanical constraints of solid/liquid food ingestion. Meal intake also modified several times the temperature of the gastric contents.

This was however seen to have no effect on the cohesion between the two capsule layers. Separation between the two layers was not observed in any of the 10 subjects, neither during the gastric residence period of the floating capsules nor in the intestine. Considering this last possibility, it is noted that, as a consequence of prolonged gastric residence, all bilayer capsules were emptied after part of their drug layers had been eroded into the stomach. This in turn reduces the eventuality of layer separation at the time of emptying or of significant spreading of the drug layer (size/shape modification) when the dosage form is swept away by the peristaltic motility of the intestinal tract. This last phenomenon had indeed been observed during the previous session with breakfast only due to the short gastric residence times obtained.

In the present study, all bilayer capsules remained monolithic from the start until the end of the monitoring procedure.

EROSION OF DRUG LAYER

The first sets of scintiphotos usually showed an initial size increase of the drug layer region of interest, this spreading of activity around the layer being only assignable to the release of 111In from the formulation. From then on, the free released activity continuously surrounded the drug layer and unfortunately impeded the realization of precise dimensional measurements and to hence confirm the preponderance of erosion during the release process. It may, however, be assumed that, as measured in vitro, the release of 111In was mainly determined in vivo by the progressive erosion of the layer formulation.

Erosion occurred in vivo and was clearly visualized for several subjects as a superficial activity burst from the drug layer and a momentary increase of 111In release after each meal administration. This sudden erosion is believed due to the mechanical constraints produced by food ingestion and proves the relative dependence of the formulation erosion rate on external agitation; as previously found in in vitro experimentation. During postprandial periods, no sudden erosion of the drug layer was found since, consistent with the results of previous session, the capsules seemed to be protected against the mixing and propelling waves of peristaltism by their residence level in the upper part of the stomach.

Individual measurements of the radioactivity remaining in the drug layer as last image before gastric emptying are given in Table 7 (mean±SD: 15±10%, n=9). The amount of 111In which has not been released from the drug layer at the time of gastric emptying appears to be generally low; this being certainly the most important consequence of the prolonged gastric residence times obtained.

It was found that two subjects (No 14, 16) emptied their capsules with no detectable amount of 111In remaining attached to the capsule and that their drug layers must therefore have been totally eroded inside the stomach. Another subject (No 17) showed in the same way total erosion of its drug layer shortly after the capsule had reached the small intestine.

In some subjects, for example No 13 and 18, the remainder of drug layer activity at emptying time was relatively high compared to the previous ones (respectively 19% and 26%) but their gastric residence times were also consistently and shortests of all study results (respectively 398 and 404 min).

It could nevertheless be observed that other subjects with longer residence times, such as No 11 and 15 who had a gastric residence time superior to 900 min, also displayed a relatively high final activity contents in their drug layers (respectively 13% and 20%). One may assume that the drug layers of these two subjects might have been submitted to less mechanical constraints inside the stomach and therefore eroded on average at a slower rate. The in vitro measured radioactivity release kinetics of the drug layer indeed show that, without stirring of the fluid medium, the release of 111In becomes very slow at about 8 hours after immersion and that more than 15% of the total radioactivity dose remains at that time in the layer formulation.

TABLE 6

Individual gastric residence time results (min) shown by the floating capsules (type Coni-Snap Supro size B).
Study conditions:
Healthy male subjects in upright position having taken a breakfast only (No 1 to 10) or having been fed with a succession of meals (No 11 to 20).

| BREAKFAST ONLY | | SUCCESSION OF MEALS | |
|---|---|---|---|
| Subject No | GASTRIC RESIDENCE TIME (min) | Subject No | GASTRIC RESIDENCE TIME (min) |
| 1 | 100 | 11 | >900 |
| 2 | 155 | 12(*) | 302 |
| 3 | 205 | 13 | 398 |
| 4 | 304 | 14 | 779 |
| 5 | 122 | 15 | >900 |
| 6 | 291 | 16 | 507 |
| 7 | 225 | 17 | 473 |
| 8 | 195 | 18 | 404 |
| 9 | 197 | 19 | 729 |
| 10(*) | 118/229 | 20 | 476 |
| Mean: | 199 | Mean: | 618 |
| ± SD: | 69 | ± SD: | 208 |
| CV (%): | 35 | CV (%): | 34 |
| Median: | 197 | Median: | 507 |
| **P < 0.001 | | | |

(*)Not taken into account for calculation.
**Significance level of GRT difference between the two session groups (two-tailed paired t-test of Student).

TABLE 7

Cytotec placebo bi-layer floating capsule
Individual results of scintigraphic monitoring (succession of meals, subjects 11 to 20).

| Subject No | Gastric Residence Time (Min) | Separation of Layers (Y/N) | Total Erosion of Drug Layer (Time/Min) | Activity Remaining in Drug Layer at Last Image Before Emptying |
|---|---|---|---|---|
| 11 | >900 | N | — | 13% |
| 12 (Discarded) | (302) | N | — | (25%) |
| 13 | 398 | N | — | 19% |
| 14 | 779 | N | 505 | 1% |
| 15 | >900 | N | — | 20% |
| 16 | 507 | N | 507 | 0% |
| 17 | 473 | N | — | 26% |
| 18 | 404 | N | — | 26% |
| 19 | 729 | N | 757 | 11% |
| 20 | 476 | N | — | 19% |
| Mean ± SD: | | 618 ± 208 Min | | 15 ± 10% |

The practice of the present invention is further illustrated by the following examples which are not intended to be limiting.

EXAMPLE No. 1

These examples illustrate some parameters influencing the release rate from the bilayer floating capsules.

| | A. Influence of HPMC K4M content | | | | | |
|---|---|---|---|---|---|---|
| FORMULATION | A | B | C | D | E | F |
| RELEASE LAYER | | | | | | |
| Misoprostol/HPMC 1:100 | 40.0 mg | 40.0 mg | 40.0 mg | 40.0 mg | 40.0 mg | 40.0 mg |
| Methocel K4M | 7.0 | 14.0 | 19.0 | 24.0 | 29.0 | 33.0 |
| Lactose | 95.0 | 83.2 | 63.4 | 53.5 | 43.6 | 34.7 |
| Stearate Mg | 2.9 | 2.7 | 2.5 | 2.4 | 2.3 | 2.2 |
| Aerosil 200 | 0.1 | 0.1 | 0.1 | 0.1 | 0.1 | 0.1 |
| FLOATING LAYER | | | | | | |
| HPMC K4M | 216 mg | | | | | |
| Lactose | 40.4 mg | | | | | |
| Stearate Mg | 13.5 mg | | | | | |

-continued

| A. Influence of HPMC K4M content | | | | | | |
|---|---|---|---|---|---|---|
| FORMULATION | A | B | C | D | E | F |
| Aerosil 200 | 0.1 mg | | | | | |

The bilayer capsules are prepared in Coni Snap Supro B hard gelatin capsule (length of the capsule = 14.4 mm, the diameter = 8.4 mm). The release layer is volumetrically filled into size 4 hard gelatin capsules. The hard gelatin capsule size 4 containing the misoprostol is emptied in the capsule and the powder is packed down. The floating layer is then volumetrically added to the capsule.

The release of misoprostol from the bilayer capsules is determined using the paddle method USP N°2 at 50 rpm 37° C. The dissolution medium is deionized water.

| FORMULATION | A | B | C | D | E | F |
|---|---|---|---|---|---|---|
| Time hours | | | % Released | | | |
| 1 | 43.3 | 23.8 | 20.8 | 19.2 | 15.1 | 14.8 |
| 3 | 78.7 | 69.3 | 47.1 | 43.9 | 34.9 | 35.3 |
| 6 | 81.8 | 87.0 | 71.9 | 69.7 | 56.4 | 58.4 |

The higher the concentration in HPMC K4M, the slower the release rate.

| B. Influence of HPMC K100 content | | | | |
|---|---|---|---|---|
| FORMULATION | G | H | I | J |
| RELEASE LAYER | | | | |
| Misoprostol/HPMC 1:100 | 40.0 | 40.0 | 40.0 | 40.0 |
| Methocel K100 | 21.0 | 27.0 | 33.0 | 38.0 |
| Lactose | 76.1 | 65.2 | 54.3 | 44.4 |
| Stearate Mg | 2.8 | 2.7 | 2.6 | 2.5 |
| Aerosil 200 | 0.1 | 0.1 | 0.1 | 0.1 |
| FLOATING LAYER | | | | |
| HPMC K4M | 216 mg | | | |
| Lactose | 40.4 mg | | | |
| Stearate Mg | 13.5 mg | | | |
| Aerosil 200 | 0.1 mg | | | |

The preparation and the dissolution conditions were conducted as described in A

| FORMULATION | G | H | I | J |
|---|---|---|---|---|
| Time hours | | % Released | | |
| 1 | 32.9 | 30.1 | 19.0 | 17.1 |
| 3 | 78.6 | 69.4 | 70.2 | 63.2 |
| 6 | 98.1 | 96.5 | 84.8 | 77.8 |

The higher the concentration in Methocel K100, the slower the release. A hydroxypropylmethylcellulose of lower viscosity such as Methocel K100 provides a faster release rate when compared to Methocel K4M of higher viscosity.

| C. Comparison of various hydrocolloids | | | | | |
|---|---|---|---|---|---|
| FORMULATION | K | L | M | N | O |
| RELEASE LAYER | | | | | |
| Misoprostol/HPMC 1:100 | 20.0 | 20.0 | 20.0 | 20.0 | 20.0 |
| Glucose | 60.0 | 60.0 | 60.0 | | 60.0 |
| Pharmacoat 606 | 60.0 | | | | |
| Pharmacoat 603 | | 60.0 | | | |
| Cryogel | | | 60.0 | | |
| CMC Na 7LF | | | | 120.0 | |
| CMC Na 7LF | | | | | 60.0 |
| Methocel K100 | | | | | |
| FLOATING LAYER | | | | | |
| Methocel K4M | 182 mg | | | | |
| PEG 6000 | 60.4 mg | | | | |
| Stearate Mg | 6.3 mg | | | | |

-continued

| C. Comparison of various hydrocolloids | | | | | |
|---|---|---|---|---|---|
| FORMULATION | K | L | M | N | O |
| Aerosil 200 | 1.3 mg | | | | |

The bilayer capsules were prepared as in example A. The floating layer was produced by granulation of Methocel K4M with melted polyethylene glycol (PEG) 6000, the mixture was cool down under stirring conditions, sieved and blended with Mg stearate and Aerosil 200.

The release of misoprostol from the bilayer capsules was determined using the paddle method USP N°2 at 0 rpm 37° C., 1 min at 50 rpm before sampling. The dissolution medium was deionized water.

| FORMULATION | K | L | M | N | O |
|---|---|---|---|---|---|
| Time hours | | | % Released | | |
| 1 | 24.4 | 60.1 | 22.8 | 9.6 | 34.2 |
| 2 | 47.0 | 82.7 | 49.3 | 53.8 | 67.3 |
| 3 | 67.7 | 84.8 | 59.7 | 71.3 | 89.0 |
| 4 | 81.8 | 88.3 | 69.3 | 80.5 | 85.2 |

By using hydrocolloids of low viscosity, high release rate can be obtained while maintaining non-disintegrating dosage forms. The dissolution is conducted at 0 rpm. This condition gives a better image of the low stirring conditions in the upper part of the stomach.

| D. Influence of formulation additives | | | | | |
|---|---|---|---|---|---|
| FORMULATION | P | Q | R | S | T |
| RELEASE LAYER | | | | | |
| Misoprostol/HPMC 1:100 | 20.2 | 20.2 | 20.2 | 20.2 | 20.2 |
| Methocel K4M | 4.0 | 4.0 | 4.0 | 4.0 | 4.0 |
| Methocel K100 | 10.0 | 10.0 | 10.0 | 10.0 | 10.0 |
| Pharmacoat 606 | 16.0 | 16.0 | 16.0 | 16.0 | 16.0 |
| Stearate Mg | 1.4 | 1.4 | 1.4 | 1.4 | 1.4 |
| Aerosil 200 | 0.2 | 0.2 | 0.2 | 0.2 | 0.2 |
| Lactose | 88.2 | 81.2 | 60.2 | 81.2 | 85.4 |
| Primogel | | 7.0 | | | |
| Avicel PH103 | | | 28.0 | | |
| PVP XL | | | | 7.0 | |
| Sodium laurylsulfate | | | | | 2.8 |
| FLOATING LAYER | | | | | |
| Methocel K4M | 216 mg | | | | |
| Lactose | 40.4 mg | | | | |
| Stearate Mg | 13.5 mg | | | | |
| Aerosil 200 | 0.1 mg | | | | |

The bilayer capsules were prepared as in Example A.

The release of misoprostol from the bilayer capsules was determined using the paddle method USP N°2 at 25 rpm 37° C. The dissolution medium was deionized water+Methocel E5 1%.

| FORMULATION | P | Q | R | S | T |
|---|---|---|---|---|---|
| Time hours | | | % Released | | |
| 1 | 22.0 | 6.6 | 9.6 | 8.5 | 5.2 |

-continued

| FORMULATION Time hours | P | Q | R | S | T |
|---|---|---|---|---|---|
| | | | % Released | | |
| 2 | | 42.6 | 16.8 | 22.2 | 20.2 | 21.8 |
| 3 | | 57.4 | 32.9 | 38.2 | 30.9 | 47.3 |
| 4 | | 87.0 | 44.4 | 49.7 | 48.3 | 62.1 |

Adjunction of some formulation additives can be used to modulate the release profiles of misoprostol.

Example No 2:
Study of the erosion rate of the drug layer for various formulations.

| FORMULATION | U | V | W | X |
|---|---|---|---|---|
| RELEASE LAYER | | | | |
| Misoprostol/HPMC 1:100 | 20.0 | 20.0 | 20.0 | 20.0 |
| Methocel K100 | 13.5 | 20.0 | 10.0 | 13.5 |
| Pharmacoat 606 | 20.0 | 20.0 | 16.0 | 20.0 |
| Stearate Mg | 2.7 | 2.7 | 2.7 | 2.7 |
| Aerosil 200 | 0.1 | 0.1 | 0.1 | 0.1 |
| Methocel K4M | | | | 4.0 |
| Lactose | 78.7 | 72.2 | 82.2 | |
| Lactose DC21 | | | | 78.7 |
| FLOATING LAYER | | | | |
| Methocel K4M | 216.0 mg | | | |
| Lactose | 40.4 mg | | | |
| Stearate Mg | 13.5 mg | | | |
| Aerosil 200 | 0.1 mg | | | |

The preparation and the dissolution conditions were as described in Example 1.A.

To study the erosion mechanism, the volume kinetics of the drug layer is performed. The size evolution of the release layer is determined using a microscope system. The capsules are immersed in a USP n°2 dissolution test vessel, the stirring rate of the paddle was 60 rpm. Dissolution media was aqueous HCl at pH3.0+0.05% tween 80 (1200 ml, 37° C.).

| FORMULATION Time min | U | V | W | X |
|---|---|---|---|---|
| | | Volume (mm3) | | |
| 0 | 155 | 155 | 155 | 155 |
| 10 | 151 | 149 | 114 | 184 |
| 20 | 151 | 136 | 96 | 112 |
| 30 | 105 | 116 | 75 | 93 |
| 45 | 72 | 109 | 61 | 64 |
| 60 | 45 | 80 | 49 | 12 |
| 90 | 16 | 50 | 32 | 0 |
| 120 | 0 | 36 | 20 | 0 |
| 180 | 0 | 9 | 0 | |
| 240 | | 0 | | |

Using this technique, the rate of erosion can be well defined. The volume kinetics indicate a continuous erosion of the drug release layer until its total disappearance. No significant disintegration of this layer is observed. Formulation X presents the faster erosion rate and is characterized by an initial volume increase. Formulation V is the slowest.

The dissolution rate was determined, as described in Example 1.A.

| FORMULATION Time hours | U | V | W | X |
|---|---|---|---|---|
| | | % released | | |
| 1 | 33 | 26 | 34 | 44 |
| 3 | 80 | 71 | 75 | 84 |
| 6 | 93 | 88 | 79 | |

After one hour there is already 44% released for formulation X and only 26% released for formulation V.

Example No 3:
Influence of floating layer formulations on floating properties of the bilayer capsules.

| FORMULATION | F1 | F2 | F3 |
|---|---|---|---|
| RELEASE LAYER | | | |
| BCG/HPMC 1:100* | 20.0 | 20.0 | 20.0 |
| Pharmacoat 606 | 16.0 | 16.0 | 16.0 |
| Methocel K100 | 10.0 | 10.0 | 10.0 |
| Methocel K4M | 4.0 | 4.0 | 4.0 |
| Lactose | 82.2 | 82.2 | 82.2 |
| Mg stearate | 2.7 | 2.7 | 2.7 |
| Aerosil 200 | 0.1 | 0.1 | 0.1 |
| FLOATING LAYER | | | |
| Methocel K4M | 216 | 182 | 160 |
| Lactose | 40.4 | | |
| PEG 6000 | | 60.4 | |
| Stearyl alcohol | | | 82.4 |
| Mg stearate | 13.5 | 6.3 | 6.3 |
| Aerosil 200 | 0.1 | 1.3 | 1.3 |

*Bromocresol green/HPMC 1:100 was used as a model drug in these examples.

Floating layer F1 was produced by a simple mix of all the excipients of the floating layer. Floating layer F2 and F3 were produced by granulation of Methocel K4M with melted PEG or Stearyl alcohol. The mixture was cooled down under stirring conditions, sieved and blended with Mg stearate and Aerosil 200. The bilayer capsule was then prepared as in Example 1.A.

The method of monitoring the total force F acting vertically on an immersed object used to study the floating properties of buoyant dosage forms, is described in detail in U.S. patent application Ser. No. 07/289,841. The force F determines the resultant-weight of an immersed object. The magnitude and the direction of the resultant force correspond to the sum of the buoyancy and the gravity forces acting on the object. If the resultant-weight is positive and high, this shows good buoyant properties, if the resultant-weight is negative, the dosage form is sinking. A decrease of the value of the resultant-weight as a function of time implies reduction of buoyancy capabilities.

| FORMULATION Time min | F1 | F2 | F3 |
|---|---|---|---|
| | | Resultant weight (mg) | |
| 0 | 166 | 166 | 145 |
| 5 | 173 | 173 | 155 |
| 10 | 178 | 181 | 136 |
| 30 | 212 | 194 | 143 |
| 60 | 210 | 170 | 140 |
| 120 | 207 | 160 | 137 |
| 240 | 194 | 148 | 129 |
| 360 | 183 | 130 | 123 |
| 480 | 170 | 120 | 120 |

All the three formulations of floating layer present good buoyant properties, formulation F1 being the best.

The diametral size of buoyancy layer F1 and its evolution as a function of time was also determined using a microscopic method. Those data show that the initial diameter is 8.4 mm and it increases to 10 mm within the 10 first minutes. This diameter remains higher than 10 mm for at least 8 hours in vitro.

What is claimed is:

1. An orally administrable sustained release pharmaceutical dosage form comprising a capsule which includes a non-compressed bilayer formulation comprising:

a drug release layer comprising the prostaglandin drug misoprostol in an amount of about 0.01 to about 1 percent by weight and a pharmaceutically acceptable vehicle, the drug release layer adapted to release the misoprostol over an extended period of time; and a floating layer providing buoyancy to said bilayer formulation;

said floating layer and drug release layer each including a hydrocolloid selected from the group consisting of HPMC, gums, polysaccharides and gelatin which, upon contact with gastric fluid, forms gelatinous mass, sufficient for cohesively binding the drug release layer and floating layer;

the pharmaceutical dosage form providing extended gastric residence time of said bilayer formulation whereby substantially all of the release of the misoprostol occurs in the stomach over an extended period of time.

2. A sustained release pharmaceutical oral dosage form including a drug and adapted to release said drug over an extended period of time, said pharmaceutical dosage form comprising a capsule including an uncompressed bilayer formulation, one layer comprising a non-disintegrating drug release layer and the other layer comprising a buoyant, floating layer; said drug release layer comprising: About 14.0% misoprostol and hydroxypropylmethyl cellulose in the ratio of 1:100; about 42.0% of a very low viscosity hydroxypropylmethylcellulose having a viscosity of about 3-5 cts for a 2% water solution at 20° C.; about 42% lactose; and about 1.0% magnesium stearate; said buoyant, floating layer comprising: about 73% of a low viscosity hydroxypropylmethyl cellulose having a viscosity of about 100 cts for a 2% solution at 20° C.; about 2.5% magnesium stearate; and about 0.6% silicone dioxide; the initial density of said pharmaceutical dosage form being about 0.6.

3. The sustained release pharmaceutical dosage form of claim 1 wherein said pharmaceutical dosage form is buoyant in gastric fluid for a period of about at least five hours.

4. The sustained release pharmaceutical dosage form of claim 1 wherein the initial density is less than one and wherein the density remains at from about 0.5 to 0.9 until said dosage form is expelled.

5. A sustained release pharmaceutical oral dosage form including a drug and adapted to release said drug over an extended period of time, said pharmaceutical dosage form comprising a capsule including an uncompressed bilayer formulation, one layer comprising a non-disintegrating drug release layer and the other layer comprising a buoyant, floating layer; said drug release layer comprising: the prostaglandin misoprostol thereof in an amount of from about 0.01 to 1% w/w;

a high viscosity hydrocolloid selected from hydroxypropylmethylcellulose, gums, polysaccharides or gelatin in an amount of from about 0 to 30%;

a low viscosity hydrocolloid selected from hydroxypropylmethylcellulose, gums, polysaccharides or gelatin in an amount of from about 0 to 80%;

a lubricant in an amount of from about 1-10%;

a diluent in an amount of from about 0-75%; and a surfactant, glidant or disintegrant in an amount of about 0.05 to 20%;

said buoyant, floating layer comprising: a high viscosity hydrocolloid in an amount of from about 30 to 95% w/w;

a lubricant in an amount of from about 0 to 15%;

a diluent in an amount of from about 0 to 60%; and a surfactant, glidant or disintegrant in an amount of about 0.05 to 2%;

said pharmaceutical dosage form providing extended gastric residence time of said bilayer formulation whereby substantially all of said misoprostol is released in the stomach over an extended period of time; said capsule having a relatively large diameter in relation to its size and an initial density of less than one.

6. The sustained release pharmaceutical dosage form of claim 5 wherein:

the high and low viscosity hydrocolloid is selected from the group consisting of hydroxypropylmethylcellulose, gums, polysaccharides and gelatin;

the lubricant is a stearate salt;

the diluent is selected from the group consisting of lactose, sorbitol, mannitol, glucose, microcrystalline cellulose, gelatin, starch, dicalcium phosphate, polyethylene glycol or polyvinyl pyrolidone; and the glidant is silicone dioxide.

7. The sustained release pharmaceutical dosage form of claim 5 wherein the ratio of misoprostol to hydrocolloid is about 1:100.

8. The sustained release pharmaceutical dosage form of claim 1 wherein the misoprostol is combined in admixture with aspirin, diclofenac, piroxicam, ibuprofen or naproxen.

9. The sustained release pharmaceutical dosage form of claim 8 wherein the misoprostol is combined with diclofenac.

10. The sustained release pharmaceutical dosage form of claim 9 wherein the misoprostol is present in an amount of from about 100 to 200 micrograms and the diclofenac is present in an amount of from about 25 to 75 milligrams.

* * * * *

UNITED STATES PATENT AND TRADEMARK OFFICE
CERTIFICATE OF CORRECTION

PATENT NO. : 5,232,704
DATED : August 3, 1993
INVENTOR(S) : Franz, et al.

It is certified that error appears in the above-indentified patent and that said Letters Patent is hereby corrected as shown below:

Column 1, line 9, reading "extended of period" should read -- extended period --.

Column 2, line 19, reading "Conference on pharmaceutical" should read -- Conference on Pharmaceutical --.

Column 14, line 22, reading "coffe-milk-sugar" should read -- coffee-milk-sugar --.

Column 20, line 20, reading "cool down" should read -- cooled down --.

Column 23, line 12, reading "forms gelatinous" should read -- forms a gelatinous --.

Signed and Sealed this

Third Day of January, 1995

Attest:

BRUCE LEHMAN

Attesting Officer  Commissioner of Patents and Trademarks